US008637219B2

(12) United States Patent
Cho et al.

(10) Patent No.: US 8,637,219 B2
(45) Date of Patent: *Jan. 28, 2014

(54) AROMATIC RING-CONTAINING COMPOUND FOR A RESIST UNDERLAYER AND RESIST UNDERLAYER COMPOSITION

(75) Inventors: Sung-Wook Cho, Uiwang-si (KR); Hwan-Sung Cheon, Uiwang-si (KR); Min-Soo Kim, Uiwang-si (KR); Seung-Bae Oh, Uiwang-si (KR); Jee-Yun Song, Uiwang-si (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 230 days.

This patent is subject to a terminal disclaimer.

(21) Appl. No.: 12/980,584

(22) Filed: Dec. 29, 2010

(65) Prior Publication Data
US 2011/0155944 A1 Jun. 30, 2011

(30) Foreign Application Priority Data
Dec. 31, 2009 (KR) .................. 10-2009-0136187

(51) Int. Cl.
G03F 7/004 (2006.01)
C07C 13/24 (2006.01)

(52) U.S. Cl.
USPC .................. 430/270.1; 430/271.1; 585/26

(58) Field of Classification Search
USPC ........... 585/24, 25, 26; 430/270.1, 271.1, 927
See application file for complete search history.

(56) References Cited

U.S. PATENT DOCUMENTS

| 4,308,360 | A | * | 12/1981 | Hall | 525/285 |
| 4,739,080 | A | * | 4/1988 | Sasaki et al. | 549/335 |
| 5,322,794 | A | * | 6/1994 | Davenport | 436/71 |
| 2008/0292995 | A1 | * | 11/2008 | Houlihan et al. | 430/322 |
| 2009/0176165 | A1 | | 7/2009 | Cheon et al. | |
| 2009/0280435 | A1 | * | 11/2009 | McKenzie et al. | 430/285.1 |
| 2011/0124498 | A1 | * | 5/2011 | Kuperman et al. | 502/221 |
| 2012/0153511 | A1 | * | 6/2012 | Song et al. | 257/786 |

FOREIGN PATENT DOCUMENTS

| JP | 62-252734 | * | 11/1987 |
| JP | 62-252734 | A | 11/1987 |
| JP | 04-297476 | A | 10/1992 |
| JP | 2001-098358 | A | 4/2001 |
| JP | 2004-158709 | A | 6/2004 |
| JP | 2008-294235 | A | 12/2008 |
| KR | 10 2006-0113884 | A | 11/2006 |
| KR | 10 2009-0068444 | A | 6/2009 |

OTHER PUBLICATIONS

Machine translation of the abstract of JP 62-252734, published on Nov. 4, 1987.*

Ioannis D. Petsalakis, Ioannis S.K. Kerkines, Nektarios N. Lathiotakis, Giannoula Theoforakopolous—Emitting and electron-transfer electronic states of tertiary amine-fluorophore sensor systems, Chemical Physics Letters, 474 (2009), pp. 278-284.*
Ulrike Rohr, Peter Schlichting, Arno Bohm, Markus Gross, Klaus Meerholz, Christoph Brauchle and Klaus Mullen—Liquid Crystalline Coronene Derivatives with Extraordinary Fluorescence Properties, Angew. Cghem. Int. Ed., 1998, 37, No. 10, pp. 1434-1437.*
English translation of JP 62-252734, published on Nov. 4, 1987.*
Zinke, et al.; "On Coronene"; Institute for Organic and Pharmaceutical Chemistry of Graz University; Nov. 23, 1946; pp. 1-5, Germany (with English translation).
Rohr, et al.; "Liquid Crystalline Coronene Derivatives with Extraordinary Flourescence Properties;" Angewandte Chemie International Edition; Jun. 5, 1998, pp. 1434-1437; vol. 37, Issue 10; WILEY-VCH Verlag GmbH; Weinheim, Germany.
Petsalakis, et al.; "Emitting and electron-transfer electronic states of tertiary amine-flourophore sensor systems;" Chemical Physics Letters; 2009; pp. 278-284; 474; Elsevier B.V.; USA.
Chinese Search Report in CN 201010613154.X, dated Jul. 16, 2013, with English translation (Cho, et al.).

* cited by examiner

Primary Examiner — Anca Eoff
(74) Attorney, Agent, or Firm — Lee & Morse, P.C.

(57) ABSTRACT

An aromatic ring-containing compound for a resist underlayer and a resist underlayer composition, the aromatic ring-containing compound being represented by the following Chemical Formula 1:

[Chemical Formula 1]

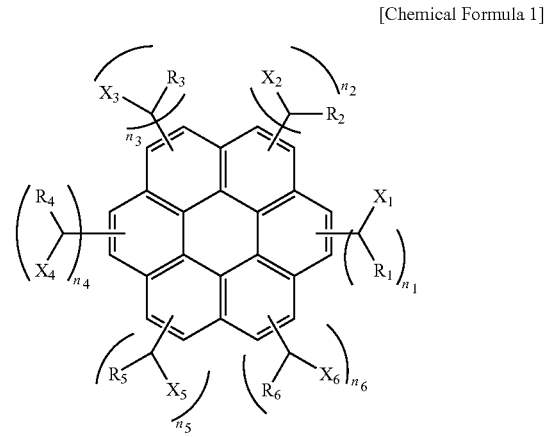

wherein, in Chemical Formula 1, $R_1$ to $R_6$ are each independently a substituted or unsubstituted C1 to C10 alkyl group, a substituted or unsubstituted C5 to C20 aromatic ring group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently hydrogen, a hydroxy group (—OH), a substituted or unsubstituted alkyl amine group, a substituted or unsubstituted alkoxy group, or an amino group (—$NH_2$), n1 to n6 are each independently 0 or 1, and $1 \leq n1+n2+n3+n4+n5+n6 \leq 6$.

14 Claims, No Drawings

AROMATIC RING-CONTAINING COMPOUND FOR A RESIST UNDERLAYER AND RESIST UNDERLAYER COMPOSITION

BACKGROUND

1. Field

Embodiments relate to an aromatic ring-containing compound for a resist underlayer and a resist underlayer composition.

2. Description of the Related Art

Reducing a size of structural shapes in the microelectronics industry and other related industries, including the manufacture of microscopic structures (e.g., micromachines and magneto-resist heads), may be desirable. In the microelectronics industry, reducing a size of microelectronic devices in order to provide a number of circuits in a given chip size may be desirable.

Effective lithographic techniques may be useful in achieving a reduction in the size of structural shapes.

A lithographic process may involve the following processes. First, a resist may be coated on an underlying material and may be subjected to exposure to irradiation to form a resist layer. Then, the resist layer may be subjected to development to provide a patterned resist layer; and the underlying material exposed in the patterned resist layer may be etched to transfer a pattern into the underlying material. After completion of the transfer, remaining portions of the resist layer may be removed.

However, the resist may not provide resistance to the etching step to an extent that is sufficient to effectively transfer the desired pattern to the underlying material. In a case in which an extremely thin resist layer is used, an underlying material to be etched is thick, a large etching depth is needed, or a particular etchant is used depending on the type of underlying material, a resist underlayer may be used.

The resist underlayer may act as an intermediate layer between the resist layer and the underlying material that to patterned by transfer from the patterned resist. The resist underlayer may receive the pattern from the patterned resist layer and may withstand etching required to transfer the pattern to the underlying material.

SUMMARY

Embodiments are directed to an aromatic ring-containing compound for a resist underlayer and a resist underlayer composition.

At least one of the above and other features and advantages may be realized by providing an aromatic ring-containing compound for a resist underlayer, the aromatic ring-containing compound being represented by the following Chemical Formula 1:

[Chemical Formula 1]

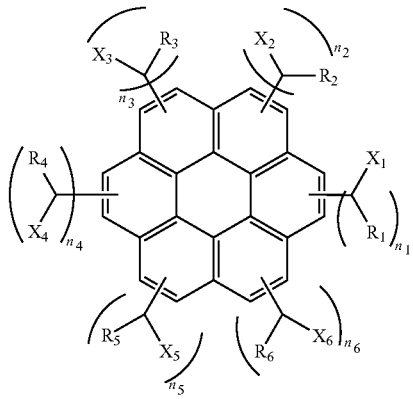

wherein, in Chemical Formula 1, $R_1$ to $R_6$ are each independently a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently hydrogen, a hydroxy group (—OH), a substituted or unsubstituted alkyl amine group, a substituted or unsubstituted alkoxy group, or an amino group (—$NH_2$), n1 to n6 are each independently 0 or 1, and $1 \leq n1+n2+n3+n4+n5+n6 \leq 6$.

At least one of $R_1$ to $R_6$ may be a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group.

The aromatic ring-containing compound may have an average molecular weight of about 500 to about 4,000.

At least one of the above and other features and advantages may also be realized by providing a resist underlayer composition including a solvent; and an aromatic ring-containing compound represented by Chemical Formula 1:

[Chemical Formula 1]

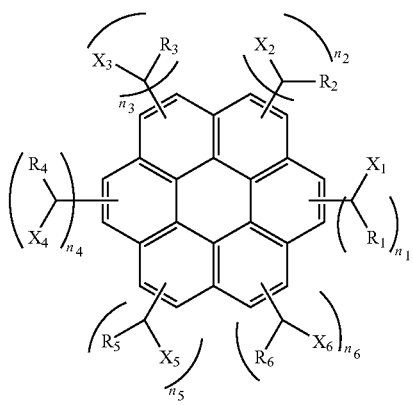

wherein, in Chemical Formula 1, $R_1$ to $R_6$ are each independently a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently hydrogen, a hydroxy group (—OH), a substituted or unsubstituted alkyl amine group, a substituted or unsubstituted alkoxy group, or an amino group (—NH$_2$), n1 to n6 are each independently 0 or 1, and $1 \leq n1+n2+n3+n4+n5+n6 \leq 6$.

At least one of $R_1$ to $R_6$ may be a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group.

The aromatic ring-containing compound may have an average molecular weight of about 500 to about 4,000.

The aromatic ring-containing compound may be included in an amount of about 1 wt % to about 20 wt %.

The aromatic ring-containing compound may be included in an amount of about 3 wt % to about 10 wt %.

The resist underlayer composition may further include a surfactant.

The surfactant may be included in an amount of about 0.01 to about 1 part by weight, based on 100 parts by weight of the resist underlayer composition.

The surfactant may include at least one of an alkyl benzene sulfonic acid salt, an alkyl pyridinium salt, polyethylene glycol, and a quaternary ammonium salt.

The resist underlayer composition may further include a cross-linking component.

The cross-linking component may be included in an amount of about 0.01 to about 1 part by weight, based on 100 parts by weight of the resist underlayer composition.

The cross-linking component may include at least one of a melamine resin, an amino resin, a glycoluril compound, and a bisepoxy compound.

DETAILED DESCRIPTION

Korean Patent Application No. 10-2009-0136187, filed on Dec. 31, 2009, in the Korean Intellectual Property Office, and entitled: "Aromatic Ring-Containing Compound for Resist Underlayer, and Resist Underlayer Composition," is incorporated by reference herein in its entirety.

Example embodiments will now be described so that this disclosure will be thorough and complete, and will fully convey the scope of the invention to those skilled in the art.

It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present.

According to an embodiment, an aromatic ring-containing compound for a resist underlayer represented by the following Chemical Formula 1 is provided.

[Chemical Formula 1]

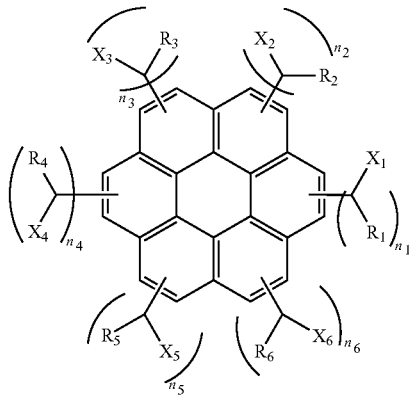

In Chemical Formula 1, $R_1$ to $R_6$ may each independently be a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ may each independently be hydrogen, a hydroxy group (—OH), a substituted or unsubstituted alkyl amine group, a substituted or unsubstituted alkoxy group, or an amino group (—NH$_2$), n1 to n6 may each independently be 0 or 1, and $1 \leq n1+n2+n3+n4+n5+n6 \leq 6$.

In Chemical Formula 1, at least one of $R_1$ to $R_6$ is preferably a substituted or unsubstituted C6 to C20 aryl group, a substituted or unsubstituted C3 to C20 cycloalkyl group or a substituted or unsubstituted C3 to C20 cycloalkenyl group, a substituted or unsubstituted C2 to C20 heteroaryl group or a substituted or unsubstituted C2 to C20 heterocycloalkyl group.

As used herein, the term "aromatic ring group" may refer to a group where electrons are delocalized or resonanced, and examples may include an aryl group, a heteroaryl group, and the like.

The term "hetero" may refer to a compound or group including 1 to 3 heteroatoms of N, O, S or P.

The alkyl amine group may be represented by —NRR', where R and R' are each independently hydrogen or a C1 to C10 linear or branched alkyl group, and both are not hydrogen.

As used herein, the term "substituted" may refer to a compound or group substituted with, e.g., a hydroxyl group, a C1 to C10 alkyl group, a C6 to C20 aryl group, or a C2 to C10 alkenyl group.

The aromatic ring-containing compound may include an aromatic ring having strong absorption at a short wavelength region (e.g., 193 nm, 248 nm, and so on). The compound may undergo a cross-linking reaction without a specific catalyst. Thus, contamination caused by a catalyst, e.g., acid, may be prevented.

The aromatic ring-containing compound may have an average molecular weight of about 500 to about 4,000. Maintaining the molecular weight of the aromatic ring-containing compound at about 500 to about 4,000 may help ensure that a desirable coating thickness or thin film is obtained.

A resist underlayer composition according to an embodiment may include the aromatic ring-containing compound of the above Chemical Formula 1 and a solvent. In an implementation, the resist underlayer composition may include a mixture of at least two compounds represented by Chemical Formula 1 and having substituents at different positions.

The solvent included in the resist underlayer composition may include any suitable organic solvent in which the aromatic ring-containing compound is sufficiently soluble. Examples of the solvent may include propyleneglycol monomethylether acetate (PGMEA), propyleneglycol monomethylether (PGME), cyclohexanone (Anone), ethyl lactate (EL), and the like.

In the resist underlayer composition according to an embodiment, the aromatic ring-containing compound may be included in an amount of about 1 to about 20 wt %. Maintaining the amount of the aromatic ring-containing compound at about 1 to about 20 wt % may help ensure that a desirable coating thickness of a resist underlayer can be appropriately adjusted. In an implementation, the aromatic ring-containing compound may be included in an amount about 3 to about 10 wt %.

The organic solvent may be used at a balance amount, e.g., about 80 to about 99 wt %. Maintaining the amount of the organic solvent at about 80 to about 99 wt % may help ensure that a desirable coating thickness of a resist underlayer can be appropriately adjusted.

The resist underlayer composition according to an embodiment may further include a surfactant or a cross-linking component. The surfactant may be included in an amount of about 0.01 to about 1 part by weight, based on 100 parts by weight of the resist underlayer composition. The cross-linking component may be included in an amount of about 0.01 to about 1 part by weight, based on 100 parts by weight of the resist underlayer composition. Maintaining the content of the cross-linking component at about 0.01 to about 1 part by weight may help ensure that an appropriate cross-linking characteristic is acquired while not changing the optical characteristic of a formed underlayer.

The surfactant may include, e.g., an alkyl benzene sulfonic acid salt, an alkyl pyridinium salt, polyethylene glycol, and/or a quaternary ammonium salt, but the embodiments are not limited thereto.

The cross-linking component may be included in order to promote a self cross-linking reaction. The cross-linking component may include any suitable cross-linking agents that react with a hydroxy group of a polymer composition by being catalyzed by a generated acid. In an implementation, the cross-linking component may include, e.g., a melamine resin, an amino resin, a glycoluril compound, and/or a bisepoxy compound.

Examples of suitable cross-linking components may include etherified amino resins, methylated melamine resins (e.g., N-methoxymethyl-melamine resins), butylated melamine resins (e.g., N-butoxymethyl-melamine resins), methylated and butylated urea resins (e.g., Cymel U-65 Resin and UFR 80 Resin), glycoluril derivatives (e.g., Powderlink 1174) represented by the following Chemical Formula A, and 2,6-bis(hydroxymethyl)-p-cresol. Bisepoxy-based compounds represented by the following Chemical Formula B and melamine-based compounds represented by the following Chemical Formula C may also be used as the cross-linking component.

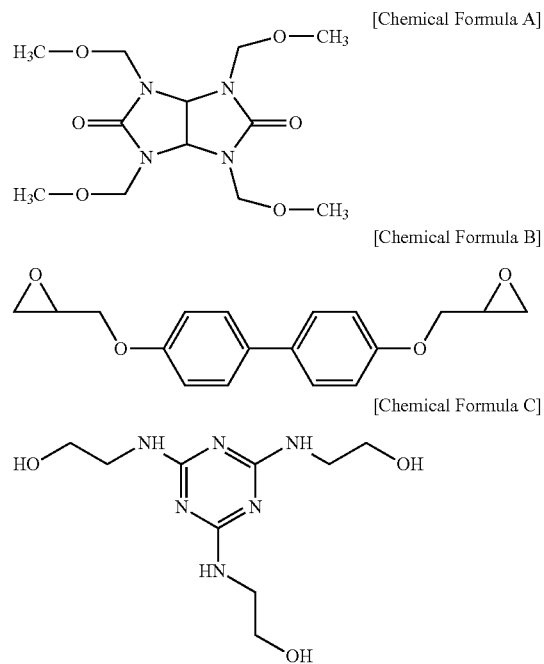

Hereinafter, a method for patterning a device using the resist underlayer composition of an embodiment is described.

First, a material to be patterned, e.g., aluminum or SiN (silicon nitride), may be formed on a silicon substrate using a suitable method. In an implementation, the material to be patterned using the resist underlayer of an embodiment may include, e.g., a conductive, semi-conductive, magnetic, or insulating material. The resist underlayer composition according to an embodiment may be spin-coated to a thickness of about 500 Å to about 4,000 Å, followed by baking at about 100° C. to about 500° C. for 10 seconds to 10 minutes to provide an underlayer. A radiation-sensitive imaging layer, e.g., a photoresist layer, may be formed on the underlayer. The imaging layer may be exposed and developed to expose regions to be patterned. Then, portions of the imaging layer and the underlayer, i.e., an anti-refractive coating layer, may be selectively removed to expose and etch a part of the material layer. For example, dry etching may be performed using a $CHF_3/CF_4$ mixed gas. After a pattern is formed on the material layer, remaining portions of the photoresist may be removed using a photoresist stripper. Accordingly, a patterned device may be provided. The device may be a semiconductor integrated circuit device.

Accordingly, the resist underlayer composition and lithographic structure prepared according to the present embodiment may be used for manufacturing and designing an integrated circuit device according to a semiconductor manufacturing process. For example, the composition and lithographic structure prepared according to an embodiment may be used for forming patterned material layer structures, such as a metal line, a hole for contact or bias, an insulation section, e.g., a damascene trench (DT) or shallow trench isolation (STI) structure, and a trench for a capacitor structure. However, the embodiments are not limited thereto.

Hereinafter, the embodiments are illustrated in more detail with reference to examples. However, they are exemplary embodiments and are not limiting. The following examples are provided to assist in a further understanding of the invention and are in no way intended to limit the scope of the invention. Embodiments that are not included herein will be readily recognized and appreciated by those skilled in the art, and thus their explanation is omitted. The following examples and experiments are given for illustrative purposes only and are not intended to limit the scope of this disclosure.

Example 1

A solution including 30.1 g (0.1 mol) of coronene, 47.1 g (0.6 mol) of acetyl chloride, and 79.8 g (0.6 mol) of trichloro aluminum dissolved in 1000 g of toluene was put into a reactor equipped with a mechanical agitator, a cooler, a 2 L 4-neck flask and was agitated followed by reaction for 10 hours. After the reaction was complete, trichloro aluminum was removed using water. To the resulting compound, 37.83 g (1.0 mol) of sodium borohydride was added followed by reaction for 17 hours. After the reaction was complete, reaction by-products were removed using a water/methanol mixture to obtain a compound of the following Chemical Formula 2 (average molecular weight=530 and $1 \leq n1+n2+n3+n4+n5+n6 \leq 6$).

[Chemical Formula 2]

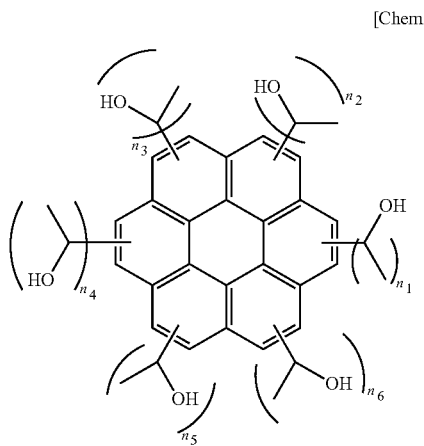

Example 2

A solution including 30.1 g (0.1 mol) of coronene, 84.32 g (0.6 mol) of benzoyl chloride, and 79.8 g (0.6 mol) of trichloro aluminum dissolved in 1000 g of toluene was put into a reactor equipped with a mechanical agitator, a cooler, a 2 L 4-neck and was agitated followed by reaction for 10 hours. After the reaction was complete, trichloro aluminum was removed using water. To the resulting compound, 37.83 g (1.0 mol) of sodium borohydride was added followed by reaction for 19 hours. After the reaction was complete, reaction by-products were removed using a water/methanol mixture to obtain a compound of the following Chemical Formula 3 (average molecular weight=910 and $2 \leq n1+n2+n3+n4+n5+n6 \leq 6$).

[Chemical Formula 3]

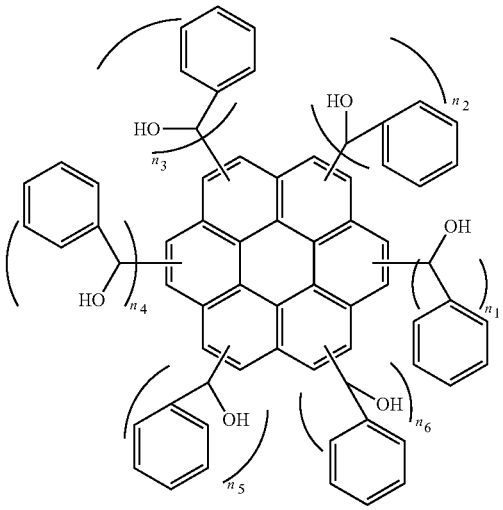

Example 3

A solution including 30.1 g (0.1 mol) of coronene, 114.01 g (0.6 mol) of 2-naphthoyl chloride, and 79.8 g (0.6 mol) of trichloro aluminum dissolved in 1000 g of toluene was put into a reactor equipped with a mechanical agitator, a cooler, a 2 L 4-neck flask and was agitated followed by reaction for 10 hours. After the reaction was complete, trichloro aluminum was removed using water. To the resulting compound, 37.83 g (1.0 mol) of sodium borohydride was added followed by reaction for 19 hours. After the reaction was complete, reaction by-products were removed using a water/methanol mixture to obtain a compound of the following Chemical Formula 4 (average molecular weight=980 and $2 \leq n1+n2+n3+n4+n5+n6 \leq 6$).

[Chemical Formula 4]

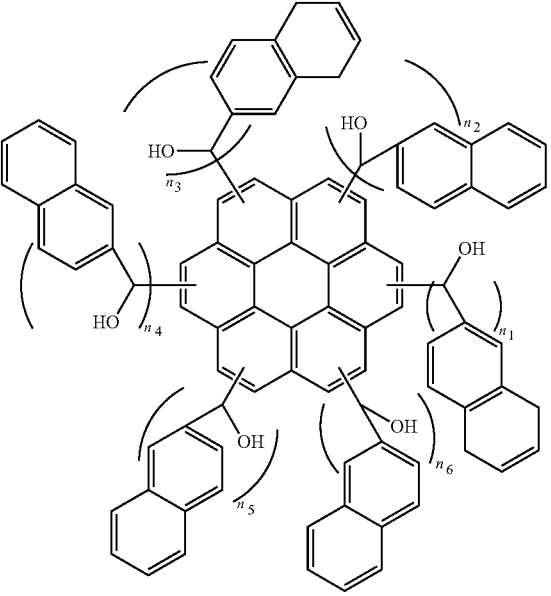

Example 4

A solution including 30.1 g (0.1 mol) of coronene, 84.31 g (0.6 mol) of cyclohexane carbonyl chloride, and 79.8 g (0.6 mol) of trichloro aluminum dissolved in 1000 g of toluene was put into a reactor equipped with a mechanical agitator, a cooler, a 2 L 4-neck flask and was agitated followed by reaction for 10 hours. After the reaction was complete, trichloro aluminum was removed using water. To the resulting compound, 37.83 g (1.0 mol) of sodium borohydride was added followed by reaction for 16 hours. After the reaction was complete, reaction by-products were removed using a water/methanol mixture to obtain a compound of the following Chemical Formula 5 (average molecular weight=1,010 and $2 \leq n1+n2+n3+n4+n5+n6 \leq 6$).

[Chemical Formula 5]

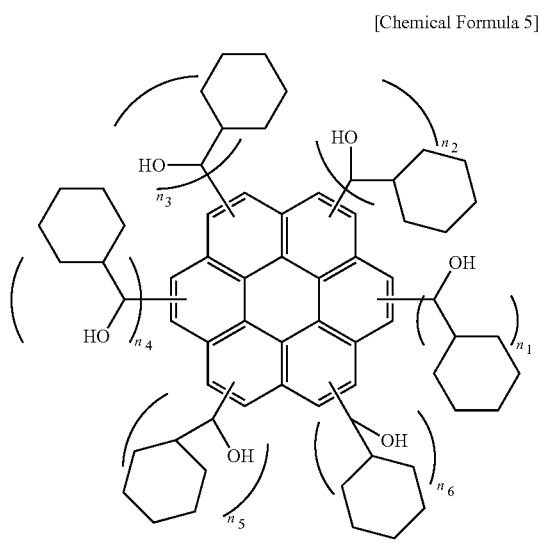

Example 5

A solution including 30.1 g (0.1 mol) of coronene, 42.16 g (0.3 mol) of benzoyl chloride, 52.01 g (0.3 mol) of 2-naphtoyl chloride, 42.16 g (0.3 mol) of cyclohexane carbonyl chloride, and 79.8 g (0.6 mol) of trichloro aluminum dissolved in 1000 g of toluene was put into a reactor equipped with a mechanical agitator, a cooler, a 2 L 4-neck and was agitated followed by reaction for 10 hours. After the reaction was complete, trichloro aluminum was removed using water. To the resulting compound, 37.83 g (1.0 mol) of sodium borohydride was added followed by reaction for 19 hours. After the reaction was complete, reaction by-products were removed using a water/methanol mixture to obtain a compound (average molecular weight=970).

Preparation of Sample Solutions

Respectively, 0.8 g of the aromatic ring-containing compounds according to Example 1 to 5 were dissolved in 9 g of propylene glycol monomethylether acetate (PGMEA) followed by filtering to provide each sample solution.

Refractive Index and Extinction Coefficient

Each sample solution including the aromatic ring-containing compound according to Examples 1 to 5 was spin-coated on a silicon wafer and baked for 60 seconds at 400° C., forming 2,500 Å-thick films. The films were measured regarding n as a refractive index and k as an extinction coefficient. The measurement was performed using an ellipsometer (J. A. Woollam Co.).

TABLE 1

| Compound used for forming a film | Optical property (193 nm) | |
|---|---|---|
| | n (refractive index) | k (extinction coefficient) |
| Example 1 | 1.27 | 0.52 |
| Example 2 | 1.29 | 0.54 |
| Example 3 | 1.28 | 0.59 |
| Example 4 | 1.25 | 0.52 |
| Example 5 | 1.28 | 0.54 |

As shown in Table 1, the sample solutions including the aromatic ring-containing compounds according to Examples 1 to 5 were identified to have a refractive index and an absorption degree suitable for use as an anti-reflection layer in an ArF (193 nm) wavelength.

Evaluation of Pattern Profile

The sample solutions including the aromatic ring-containing compounds according to Examples 1 to 5 were respectively spin-coated on a silicon wafer including SiN (silicon nitride) and baked at 400° C. for 60 seconds to form 2,500 Å-thick films. An ArF photoresist was coated on the underlayer and baked at 110° C. for 60 seconds. The resultant was exposed to light using ArF exposure equipment (ASML1250 (FN70 5.0 active, NA 0.82)) and developed with a 2.38 wt % tetramethyl ammonium hydroxide aqueous solution. Then, an 80 nm line-and-space pattern thereof was examined using an FE (field emission)-SEM. EL (expose latitude) margin depending on exposure changes and DoF (depth of focus) margin depending on distance changes from a light were measured. The results are provided in the following Table 2.

TABLE 2

| Compound used for forming an underlayer | Pattern profile | | |
|---|---|---|---|
| | EL margin ($^\Delta$CD/exposure energy mJ) | DoF margin (μm) | Profile |
| Example 1 | 4.4 | 0.23 | cubic |
| Example 2 | 4.1 | 0.24 | cubic |
| Example 3 | 3 | 0.27 | cubic |
| Example 4 | 3.5 | 0.25 | cubic |
| Example 5 | 3.5 | 0.26 | cubic |

Evaluation of Etching Performance

The sample solutions including the aromatic ring-containing compounds according to Examples 1 to 5 were respectively spin-coated on a silicon wafer including SiN (silicon nitride) and baked at 400° C. for 60 seconds to form 2,500 Å-thick films. An ArF photoresist was coated on the underlayer and baked at 110° C. for 60 seconds. The resultant was exposed to light using ArF exposure equipment (ASML1250 (FN70 5.0 active, NA 0.82)) and developed with a 2.38 wt % tetramethyl ammonium hydroxide aqueous solution. The patterned specimens were dry-etched using a $CHF_3/CF_4$ mixed gas, and dry-etched using a gas mixture of $CHF_3/CF_4$ mixed in a different selectivity ratio. All the remaining organic materials were removed using oxygen ($O_2$) gas, and then the cross-sections were observed with the FE-SEM. The observation results are as shown in Table 3.

TABLE 3

| Compound used for forming an underlayer | Pattern of underlayer after etching | Pattern of silicon nitride after etching |
| --- | --- | --- |
| Example 1 | Vertical (Anisotropic) | Vertical (Anisotropic) |
| Example 2 | Vertical (Anisotropic)) | Vertical (Anisotropic) |
| Example 3 | Vertical (Anisotropic) | Vertical (Anisotropic) |
| Example 4 | Vertical (Anisotropic) | Vertical (Anisotropic)) |
| Example 5 | Vertical (Anisotropic) | Vertical (Anisotropic) |

From the results, good patterns were obtained after the underlayer etching and the silicon nitride etching, indicating that the silicon nitride etching was performed well due to sufficient resistance against the etching gas.

Evaluation of Heat Resistance

Each sample solution including the aromatic ring-containing compound according to Examples 1 to 5 was spin-coated on a silicon wafer and baked for 60 seconds at 200° C., forming 4,000 Å-thick films. The films were baked for 120 seconds at 400° C. Thin film thickness difference between films baked at 200° C. and those baked at 400° C. was determined and outgas was observed with a naked eye.

The thin film thickness difference was calculated according to the following Equation 1.

(thin film thickness baked at 200° C.–thin film thickness baked at 400° C.)/thin film thickness baked at 200° C.×100     [Equation 1]

TABLE 4

| Compound used for film fabrication | Thin film thickness difference between 400° C. and 200° C. (%) | Outgas generation |
| --- | --- | --- |
| Example 1 | 7.8 | No |
| Example 2 | 8.5 | No |
| Example 3 | 9.2 | No |
| Example 4 | 8.3 | No |
| Example 5 | 8.7 | No |

As shown in Table 4, the films fabricated using the aromatic ring-containing compounds according to Example 1 to 5 exhibited small differences of thin film thickness difference, and released no outgas. From these results, it may be seen that the aromatic ring-containing compounds exhibited good heat resistance.

The embodiments provide an underlayer material that is easy to apply to substrates. Thus, drawbacks such as high cost associated with, e.g., chemical and physical vapor deposition, special solvents, and/or high-temperature baking, may be avoided. For example, the resist underlayer composition of an embodiment may be applied by spin-coating techniques, e.g., without high temperature baking.

The embodiments provide a resist underlayer composition that can be selectively etched using an overlying resist layer as a mask in an easy manner while being resistant to etching necessary to pattern an underlying metal layer using an underlayer as a mask. The embodiments provide a resist underlayer composition that exhibits superior storage life-span properties and avoids unwanted interactions (e.g., acid pollution from a hard mask) with an imaging resist layer. The embodiments provide a resist underlayer composition that has particular optical properties against imaging irradiation at short wavelengths (e.g., 157 nm, 193 nm, and 248 nm) also needs to be researched.

A resist underlayer prepared from the resist underlay composition of an embodiment may serve as an antireflective layer having high etching selectivity and sufficient resistance against multiple etching, as well as minimized reflectivity between a resist and underlying material, during a lithographic process. Accordingly, the lithographic process may produce a very fine semiconductor device.

The embodiments provide an aromatic ring-containing compound for a resist underlayer and a resist underlayer composition capable of being coated using a spin-on application technique, having excellent optical properties, mechanical characteristics, and etching selectivity characteristics, with minimum remaining acid content.

The resist underlayer composition of an embodiment may have a refractive index and absorption of an appropriate range as an antireflective layer in a DUV wavelength region such as ArF (193 nm). Thus, it may minimize reflectivity between the resist (irradiation-sensitive imaging layer) resist and a material layer. Accordingly, the resist underlayer composition may provide an excellent lithographic structure in terms of pattern profile or margins. The resist underlayer composition may have high etching selectivity during a lithographic process and sufficient resistance against multiple etching. Thus, an etching profile of a resist underlayer which is an image to be transferred to a lower layer may be very good.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An aromatic ring-containing compound for a resist underlayer, the aromatic ring-containing compound being represented by Chemical Formula 1:

[Chemical Formula 1]

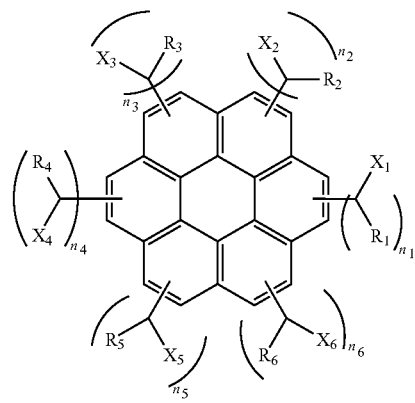

wherein, in Chemical Formula 1, $R_1$ to $R_6$ are each independently a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, provided that at least one of $R_1$ to $R_6$ is a substituted or unsubstituted C6 to C20 aryl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently a hydroxy group (—OH), a substituted or unsubstituted alkyl amine group, a substituted or unsubstituted alkoxy group, or an amino group (—$NH_2$), n1 to n6 are each independently 0 or 1, and $2 \leq n1+n2+n3+n4+n5+n6 \leq 6$.

2. The aromatic ring-containing compound as claimed in claim 1, wherein the aromatic ring-containing compound has an average molecular weight of about 500 to about 4,000.

3. The aromatic ring-containing compound as claimed in claim 1, wherein, in Chemical Formula 1:
   n1 is 1, and
   $X_1$ is a hydroxy group.

4. The aromatic ring-containing compound as claimed in claim 3, wherein $R_1$ is a substituted or unsubstituted C6 to C20 aryl group.

5. The aromatic ring-containing compound as claimed in claim 4, wherein $R_1$ is a substituted or unsubstituted C10 to C20 aryl group.

6. A resist underlayer composition, comprising:
   a solvent; and
   an aromatic ring-containing compound represented by Chemical Formula 1:

[Chemical Formula 1]

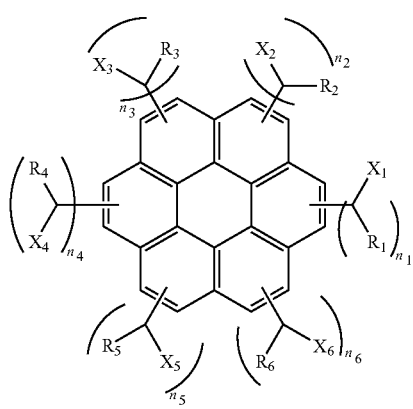

wherein, in Chemical Formula 1, $R_1$ to $R_6$ are each independently a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, provided that at least one of $R_1$ to $R_6$ is a substituted or unsubstituted C6 to C20 aryl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently a hydroxy group (—OH), a substituted or unsubstituted alkyl amine group, a substituted or unsubstituted alkoxy group, or an amino group (—$NH_2$), n1 to n6 are each independently 0 or 1, and $2 \leq n1+n2+n3+n4+n5+n6 \leq 6$.

7. The resist underlayer composition as claimed in claim 6, wherein the aromatic ring-containing compound has an average molecular weight of about 500 to about 4,000.

8. The resist underlayer composition as claimed in claim 6, wherein the aromatic ring-containing compound is included in an amount of about 1 wt % to about 20 wt %.

9. The resist underlayer composition as claimed in claim 8, wherein the aromatic ring-containing compound is included in an amount of about 3 wt % to about 10 wt %.

10. The resist underlayer composition as claimed in claim 6, further comprising a surfactant.

11. The resist underlayer composition as claimed in claim 10, wherein the surfactant is included in an amount of about 0.01 to about 1 part by weight, based on 100 parts by weight of the resist underlayer composition.

12. The resist underlayer composition as claimed in claim 10, wherein the surfactant includes at least one of an alkyl benzene sulfonic acid salt, an alkyl pyridinium salt, polyethylene glycol, and a quaternary ammonium salt.

13. A resist underlayer composition, comprising:
   a solvent;
   a cross-linking component; and
   an aromatic ring-containing compound represented by Chemical Formula 1:

[Chemical Formula 1]

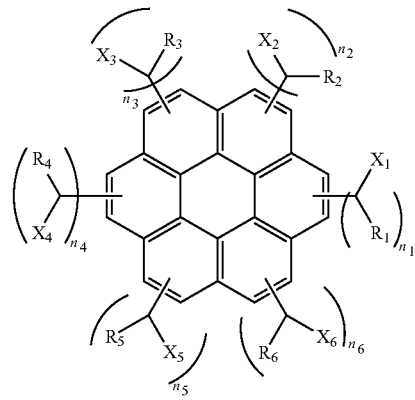

wherein, in Chemical Formula 1, $R_1$ to $R_6$ are each independently a substituted or unsubstituted C1 to C10 alkyl group, a substituted or unsubstituted C6 to C20 aryl group, a substituted or unsubstituted C3 to C20 cycloalkyl group, a substituted or unsubstituted C3 to C20 cycloalkenyl group, a substituted or unsubstituted C2 to C20 heteroaryl group, or a substituted or unsubstituted C2 to C20 heterocycloalkyl group, $X_1$ to $X_6$ are each independently hydrogen, a hydroxy group (—OH), a substituted or unsubstituted alkyl amine group, a substituted or unsubstituted alkoxy group, or an amino group (—$NH_2$), n1 to n6 are each independently 0 or 1, $1 \leq n1+n2+n3+n4+n5+n6 \leq 6$, and wherein the cross-linking component is included in an amount of about 0.01 to about 1 part by weight, based on 100 parts by weight of the resist underlayer composition.

14. The resist underlayer composition as claimed in claim 13, wherein the cross-linking component includes at least one of a melamine resin, an amino resin, a glycoluril compound, and a bisepoxy compound.

* * * * *